United States Patent [19]
Xu

[11] Patent Number: 5,603,718
[45] Date of Patent: Feb. 18, 1997

[54] SUTURING DEVICE

[75] Inventor: Zhongren Xu, Kanagawa, Japan

[73] Assignee: Terumo Kabushiki Kaisha, Tokyo, Japan

[21] Appl. No.: 413,614

[22] Filed: Mar. 30, 1995

[30] Foreign Application Priority Data

Mar. 31, 1994 [JP] Japan .................................. 6-085830

[51] Int. Cl.⁶ .................................................... A61B 17/00
[52] U.S. Cl. ......................... 606/145; 606/139; 606/147; 112/169
[58] Field of Search ............................... 606/1, 139, 144, 606/145, 147, 148, 151, 205–208; 112/169, 80.03

[56] References Cited

U.S. PATENT DOCUMENTS

| | | | |
|---|---|---|---|
| 4,109,658 | 8/1978 | Hughes | 606/145 |
| 4,597,390 | 7/1986 | Mulhollan et al. | 606/147 |
| 4,827,931 | 5/1989 | Longmore | 606/148 |
| 4,935,027 | 6/1990 | Yoon | 606/146 |
| 4,942,866 | 7/1990 | Usami | 600/148 |
| 5,100,418 | 3/1992 | Yoon et al. | 606/139 |
| 5,100,421 | 3/1992 | Christoudias | 606/147 |
| 5,366,459 | 11/1994 | Yoon | 606/151 |
| 5,470,338 | 11/1995 | Whitfield et al. | 606/144 |

FOREIGN PATENT DOCUMENTS

WO94/28801 12/1994 WIPO ................................ 606/148

*Primary Examiner*—Jeffrey A. Schmidt
*Attorney, Agent, or Firm*—Burns, Doane, Swecker & Mathis, LLP

[57] ABSTRACT

A suturing device includes a first needle retaining member for causing the basal end part of an arcuate needle to be held in place at the leading end of an insertion lever, a second needle retaining member capable of holding the leading end part of said needle, open-close mechanism swingably supporting the first needle retaining member and the second needle retaining member and switching the needle retaining members between the "close" posture in which the leading end of the needle is abutted against the leading end of the second needle retaining member and the "open" posture in which the abutting leading ends are separated to allow insertion of the needle through a trocar, and rotary mechanism for rotating the two needle retaining members in each of the "open" and "close" postures. The insertion lever is provided at the basal end thereof with a manipulating part for effecting remote control of the rotary means and the open-close means.

8 Claims, 11 Drawing Sheets

SUTURING DEVICE

BACKGROUND

1. Field of the Invention

This invention relates to a suturing device to be used mainly for surgical operations under a peritoneoscope.

2. Description of the Prior Art

In recent years, regarding the surgical operations for the excision of the appendix and the gallbladder, the operation performed under a peritoneoscope and allowed to obviate the necessity for laparotomy has been attracting attention in recent years as a prospective alternative to the conventional laparotomy. This operation under a peritoneoscope is carried out by inserting a plurality of communicating tubes called trocars through the abdominal wall into the abdominal cavity, displaying on a monitor screen the image of the interior of the abdominal cavity with the aid of a miniature camera inserted via one of the trocars, and enabling the surgeon to study the image on the screen and perform a desired surgical treatment by manipulating suitably a forceps, a scissors, an electric scalpel, and needle holder, or the like inserted via the other trocars.

In the surgical operation for suturing vital tissue under a peritoneoscope, since no suturing device has been developed for exclusive use in the surgical operation under a peritoneoscope, the surgeon has no alternative but to hold an arcuately curved needle by the use of the standard needle holder and suture the tissue under treatment with the needle. The suturing work, therefore, consumes much time and labor.

Particularly, the standard needle holder which is holding a needle therein is not allowed to change its posture. When it is fixed in a posture for holding an arcuate needle readied for suturing vital tissue so that the leading end of the needle may be directed perpendicularly to the vital tissue to be pierced therewith, this needle holder in that posture is not easily passed through the small trocar. For this reason, the arcuate needle is required to have a small radius at a sacrifice of the efficiency of the suturing operation and therefore limit sutures to those of narrow pitches. This limitation poses an obstacle to the proper performance of sutures.

Frequently, the needle holder permits no free change in the angle with which it holds a given needle and fails to plunge the needle at a proper angle into the vital tissue. In this case, the suture cannot be accurately carried out. Further, since the needle is small and deficient in operational efficiency as described above, it entrains the possibility that the needle point will not easily pierce the vital tissue and the needle will break within the vital tissue when the vital tissue to be pierced therewith is relatively tough or when the depth of piercing is large, for example. After the needle has been thrust into the vital tissue, a separately prepared forceps or the like is used to hold the leading end of the needle fast in position and allow passage of a thread therethrough. This work necessitates a change in the posture of the forceps at the cost of time and labor.

SUMMARY OF THE INVENTION

An object of this invention is to provide a suturing device which allows use of an arcuate needle of a relatively large radius, excels in efficiency of manipulation, and permits a proper suture to be easily carried out.

To accomplish the object described above according to this invention, there is provided a suturing device which comprises an elongate insertion lever to be inserted into a communicating tube for establishing communication between the interior and the exterior of the body cavity, a first needle retaining member disposed at the leading end part of the insertion lever and provided in the leading end part thereof with attach-detach means capable of detachably holding the basal end part of an arcuately curved needle, a second needle retaining member disposed in the leading end part of the insertion lever and provided at the leading end part thereof with attach-detach means capable of detachably holding the basal end part of the needle, revolving means for revolving each of the needle retaining members at an angle within a stated range relative to the insertion lever, open-close means for switching the posture of each of the first needle retaining member and the second needle retaining member between the "open" posture permitting the pertinent needle retaining member to be inserted into the communicating tube and the "close" posture permitting the leading end of the needle held by the first needle retaining member to be positioned near the leading end of the second needle retaining member, and a manipulating part disposed in the basal end part of the insertion lever and adapted to manipulate the needle retaining members, the revolving means, and the open-close means by remote control.

The suturing device of this invention allows the suturing work to be carried out very quickly because it is provided with two needle retaining members and consequently enabled to perform both the insertion of a needle into the vital tissue and the extraction of the needle from the vital tissue without requiring a change in the posture in which the needle is held by the needle retaining member.

BRIEF DESCRIPTION OF THE DRAWINGS

This invention will be better understood and the objects, features, and advantages thereof other than those set forth above will become apparent when consideration is given to the following detailed description thereof, which makes reference to the annexed drawings wherein.

DETAILED DESCRIPTION OF THE PREFERRED EMBODIMENT

Now, one embodiment of this invention will be described below with reference to the drawings.

Figure 1:
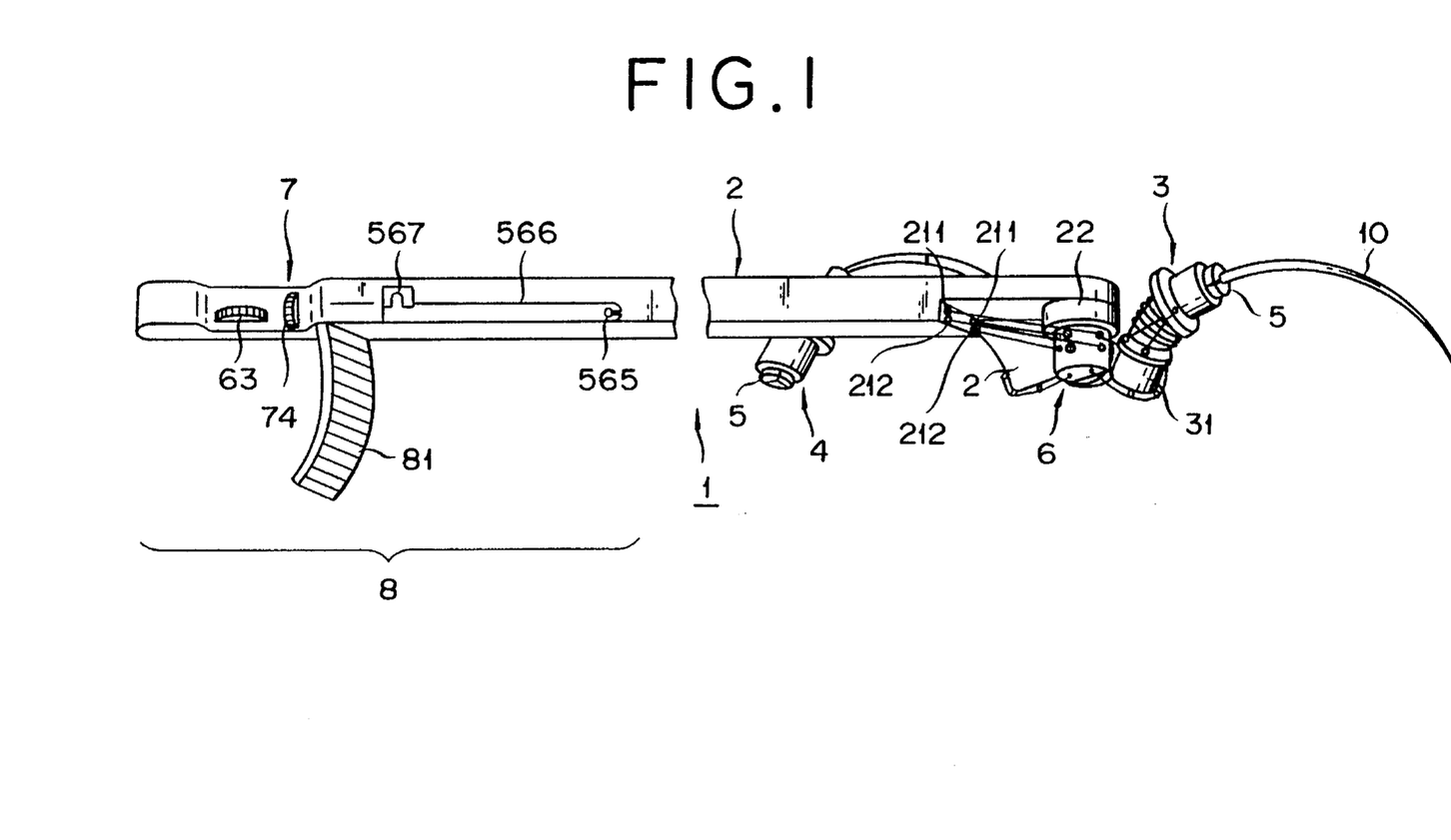
FIG. 1 is a side view showing the whole construction of a suturing device of this invention.

In the following description, the left side in FIG. 1 is referred to as "basal end" and the right side as "leading end" and the motion toward the leading end as "advance" and the motion toward the basal end as "retraction."

A suturing device 1 shown in the diagram is intended to be used for surgical operations performed under a peritoneoscope. It is put to use as inserted in a trocar (not shown), a communicating tube disposed as thrust through the abdominal wall and allowed to establish communication between the interior and the exterior of the abdominal cavity. This suturing device 1, as shown in FIG. 1, comprises an elongate insertion lever 2 for insertion into the trocar, a first needle retaining member 3 and a second needle retaining member 4 disposed in the leading end part of the insertion lever 2, revolving means 6 for supporting the first and the second needle retaining member 3 and 4 and revolving the needle retaining members 3 and 4 within angles of stated ranges, open-close means 7 for swinging the first and the second needle retaining members 3 and 4 and switching them between an "open" posture and a "close" posture, attach-detach means 5 for manipulating the attachment and detachment of a needle 10 to and from the needle retaining members 3 and 4, revolving means 6, and a manipulating part 8 having the open-close means 7 and other manipulating members disposed therein.

Figure 3:
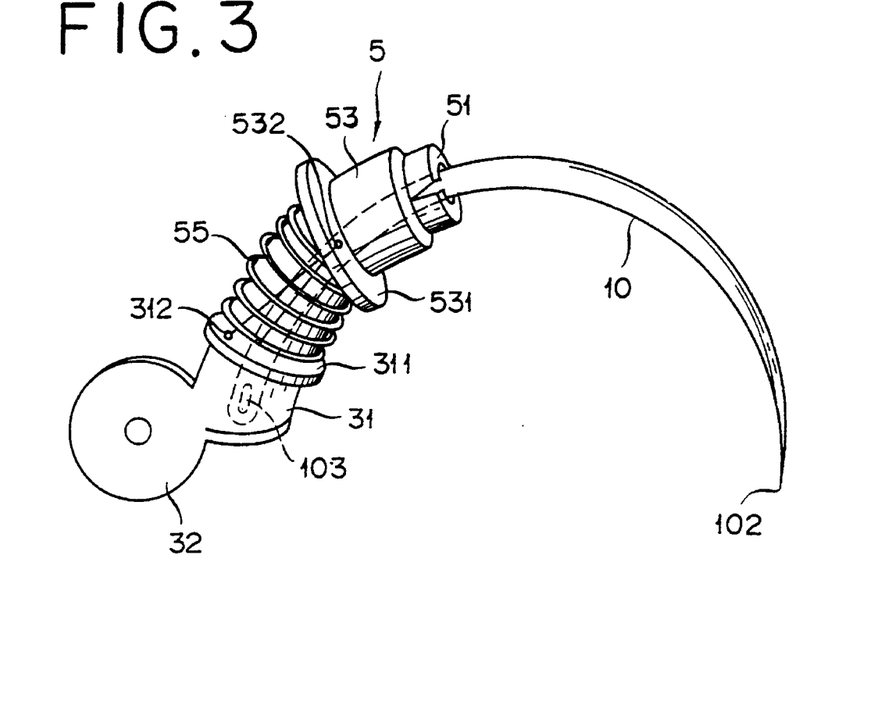
FIG. 3 is a perspective view showing the whole construction of a first needle retaining member.

The needle 10 which is used in the suturing device 1 of this invention, as shown in FIG. 3, is arcuately curved and possessed of a sharp leading end part 102. Then, in the basal end part of the needle 10, a small hole 103 for passing a suture (not shown) is formed. In this case, since the needle 10 assumes a posture shown in FIG. 1 (basic posture) when the first needle retaining member 3 supporting the needle 10 is inserted into the trocar, the arcuate needle is allowed to have a relatively large radius R of curvature, specifically a radius 0.5 to 1.5 times, preferably 0.6 to 1.2 times, the inside diameter of the trocar. As a result, the suturing work is carried out easily and the freedom of selecting a suturing pitch is augmented.

Now, the composing components of the suturing device will be described successively hereinbelow. The insertion lever 2 is a hollow tubular member. A stretching lever 564 of the attach-detach means 5, a wire 62 of the revolving means 6, a winding lever 73 of the open-close means 7 which will be specifically mentioned hereinbelow are passed therein.

Figure 2:
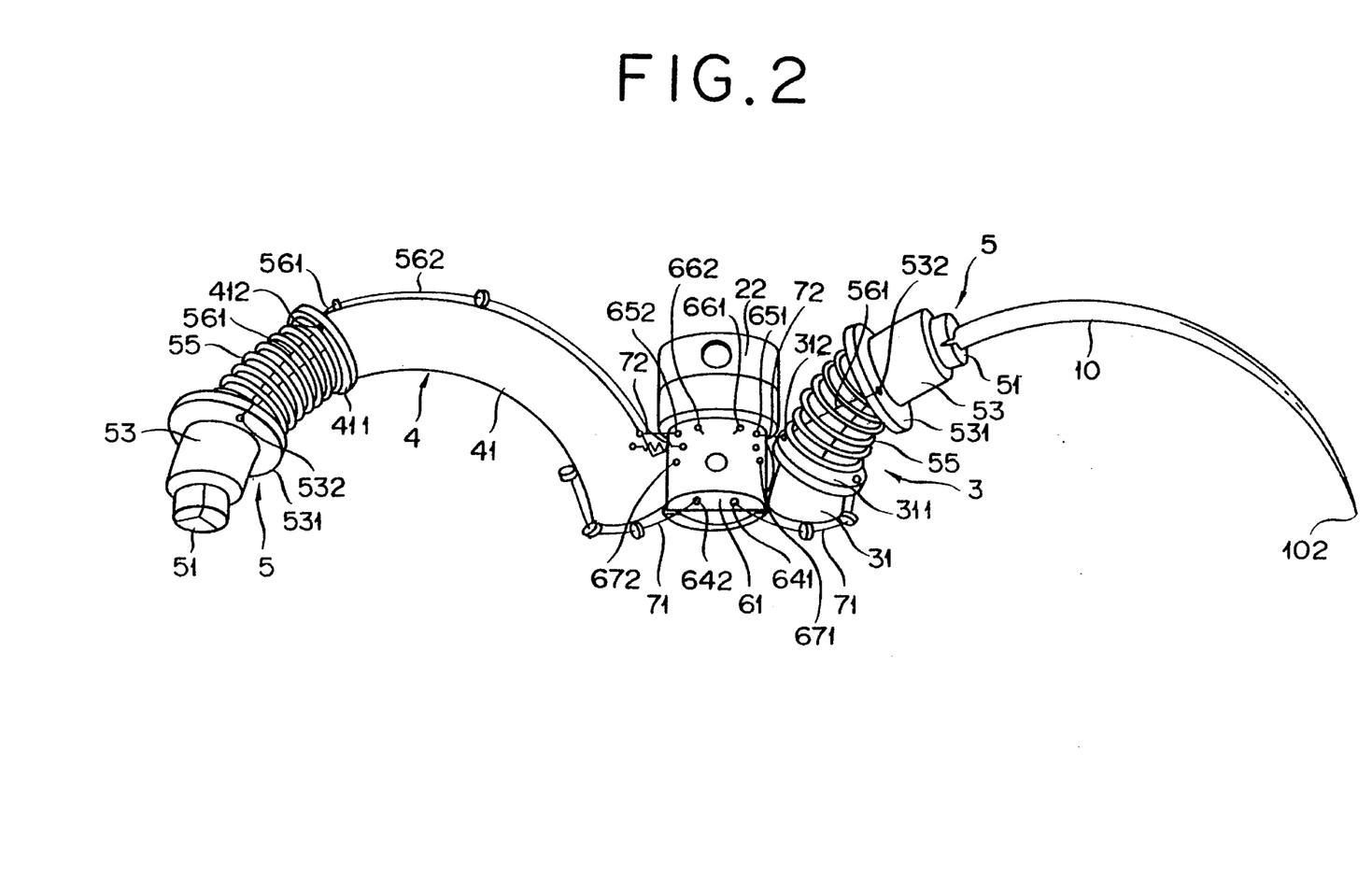
FIG. 2 is a magnified view showing the attachment part of a needle retaining member according to this invention.

In the leading end part of the insertion lever 2, a rotary body 61 of the revolving means 6 is rotatably disposed. The first needle retaining member 3 and the second needle retaining member 4 are shakeably supported on the rotary body 61. The first needle retaining member 3, as shown in FIG. 2 and FIG. 3, comprises an arcuately curved main body 31, a connecting part 32 disposed in the basal end part of the main body 31 and revolvably connected to the rotary body 61, and the attach-detach means 5 disposed at the leading end of the main body 31. Owing to this construction, the first needle retaining member 3 is capable of detachably holding the basal end part of the arcuately curved needle 10. When the basal end part of the arcuate needle 10 is held in place by the attach-detach means, the main body 31 of the first needle retaining member 3 and the needle 10 jointly form a practically semicircular shape.

Figure 4:
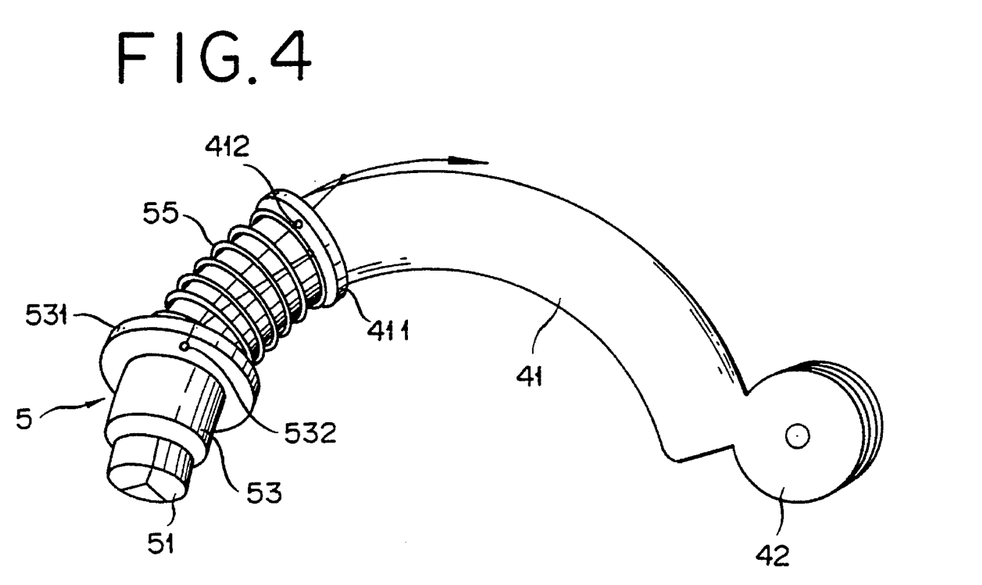
FIG. 4 is a perspective view showing the whole construction of a second needle retaining member.

The second needle retaining member 4, as shown in FIG. 2 and FIG. 4, comprises an arcuately curved main body 41, a connecting part 42 disposed in the basal end part of the main body 41 and revolvably connected to the rotary body 61, and the attach-detach means 5 disposed at the leading end of the main body 41. Owing to this construction, the second needle retaining member 4 is capable of detachably holding the leading end part of the arcuately curved needle at the detach-attach means 5 thereof.

Figure 5:
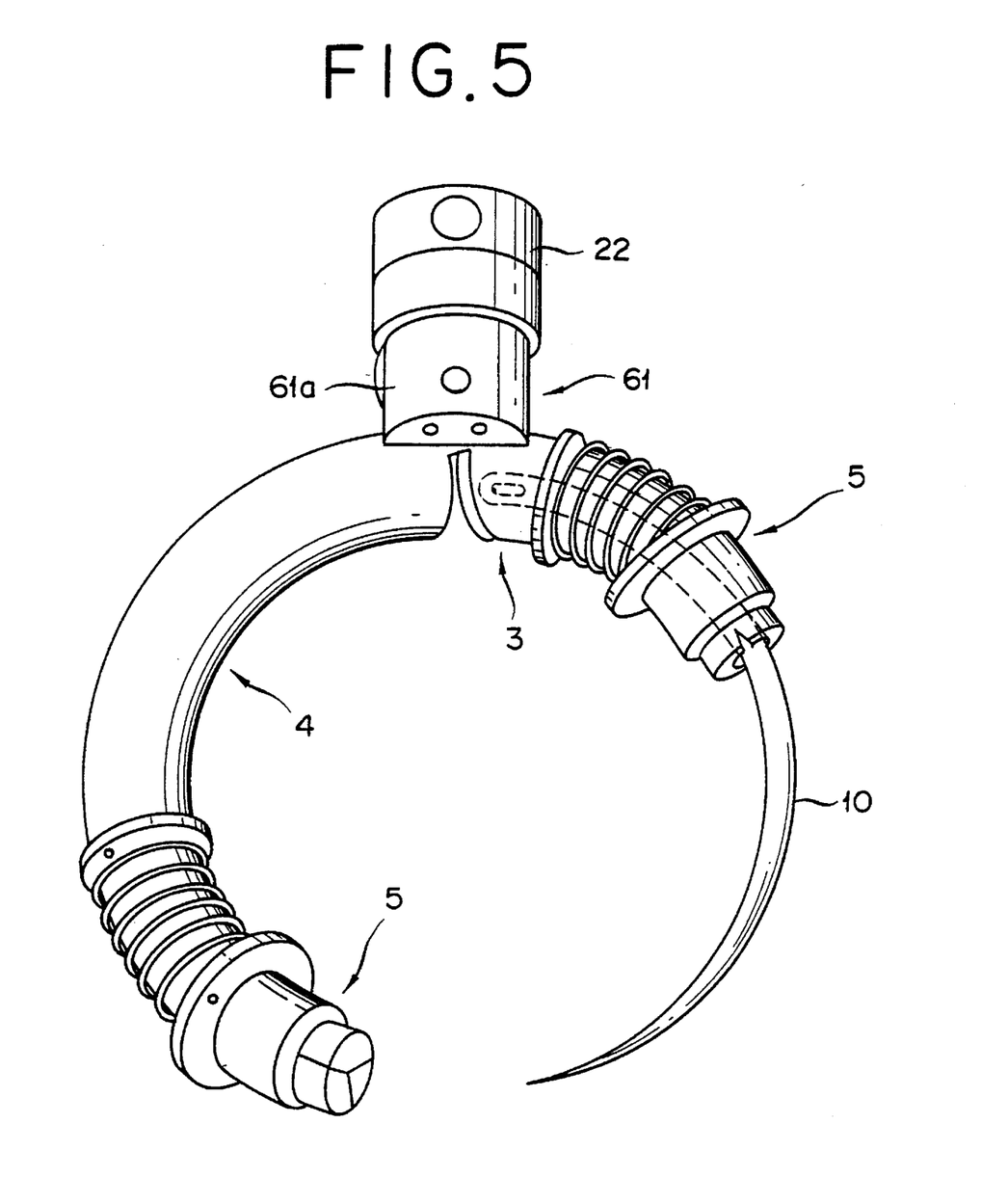
FIG. 5 is a magnified perspective view showing the needle retaining member in a state of "close" posture.

The main body 41 of the second needle retaining member 4 is formed in a greater length than the main body 31 of the first needle retaining member 3 and is made to assume a semicircular shape by itself. When the first needle retaining member 3 holding the needle 10 in place thereon and the second needle retaining member 4 are lowered below the insertion lever 2 and brought to the "close" state as shown in FIG. 5, the leading end of the needle 10 is abutted against the leading end of the attach-detach means 5 disposed at the leading end of the second needle retaining member 4 and the two needle retaining members jointly form a practically circular shape.

Figure 6:
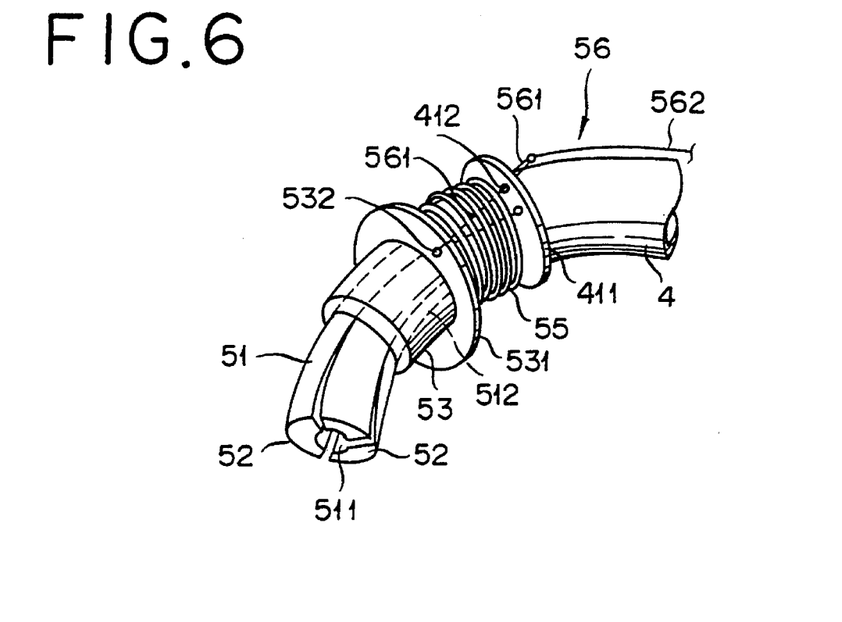
FIG. 6 is a magnified perspective view showing the construction of attach-detach means.

The attach-detach means 5 disposed one each in the leading end parts of the first needle retaining member 3 and the second needle retaining member 4, as shown in FIG. 6, comprise a chuck 51 consisting of three open-close nipping pieces 52, a ring 53 for regulating the opening motion of the chuck 51, a coil spring 55 serving as a member for urging the chuck 51 in the closing direction (in the direction of the leading end), and stretching means 56 for drawing the ring 53 in the opening direction of the chuck 51 (in the direction of the basal end) by overcoming the urging force of the coil spring 55. The basal end of the chuck 51 is fixed on the main body 31 and the main body 41.

The chuck 51 is provided in the central part thereof with a circular hole 511 for allowing insertion therein of the needle 10. On the outer circumferential surface of the chuck 51, a tapered part 512 having the outside diameter thereof gradually decreased toward the basal end thereof is formed. This tapered part 512 is inserted into the ring 53. When the ring 53 is pressed toward the leading end of the chuck 51, the nipping pieces 52 are gathered toward the center as regulated by the ring 53 and the substantial inside diameter of the hole 511 is decreased. When the ring 53 is drawn and retracted toward the basal end in spite of the urging force of the coil spring 55, the nipping pieces 52 are thrust out of the ring 53 and separated from one another and the substantial inside diameter of the hole 511 is increased to open the chuck 51.

A flange 531 is formed at the basal end of the ring 53. Coil springs 55 and 55 are interposed between the flange 531 and flanges 311, 411 formed respectively at the leading ends of the main body 31 and the main body 41.

Figure 7:
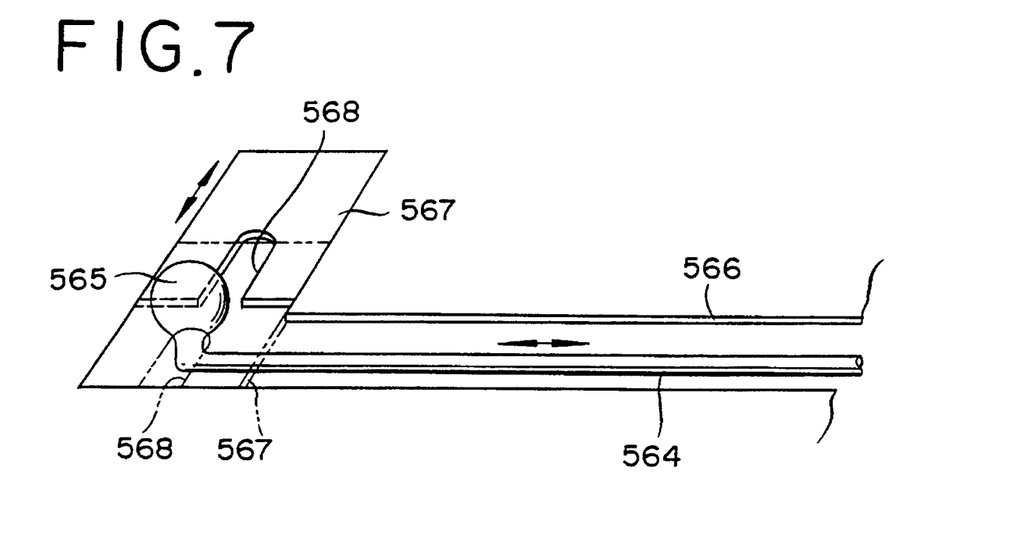
FIG. 7 is a partial magnified view of an insertion lever showing the construction of attach-detach means and stretching means.

Now, the stretching means 56 will be described below. The stretching means 56, as shown in FIG. 6 and FIG. 7, comprises first wires 561, a second wire 562, and the stretching lever 564 which are mutually connected. The two first wires 561 severally act on the ring 53 and cause the ring 53 to retract in spite of the urging force of the coil spring 55. To one end of the second wire 562 is connected one end each of the two first wires 561. The other end of the second wire 562 is passed through a hole 211 formed in the leading end part of the insertion lever 2 (see FIG. 1) and eventually connected to the leading end of the stretching lever 564. The second wire 562, as shown in FIG. 7, is used for transmitting a manipulated variable from the stretching lever 564 to the first wire 561. The stretching lever 564 is provided at the trailing end thereof with a ball 565 and is moved in the longitudinal direction along a guide part 566 which is formed in the insertion lever 2.

The guide part 566 is provided at the trailing end thereof with a regulating member 567. A notch 568 is formed at the center of the regulating member 567 and is used for fixing the stretching lever 564 at the most retracted position.

In the flange 531 of the ring 53, holes 532 are formed at the positions symmetrical across the center of the lateral cross section of the ring 53 as shown in FIGS. 3 and 4. In the flanges 311 and 411 of the main bodies 31 and 41 mentioned above, paired holes 312 and 412 are similarly formed. The leading ends of the first wires 561, as shown in FIG. 2, are passed severally through the holes 312 and 412, extended inside the coil spring 55 to reach the hole 532, turned back around the hole 532, and finally fixed in the leading end parts of the main bodies 31 and 41.

The attach-detach means 5 constructed as described above is allowed to hold the needle 10 at a desired position by means of the chuck 51 and adjust the length of protrusion of the needle 10 from the leading end of the chuck 51. Further, because of the construction, the attach-detach means 5 takes hold of the needle 10 with great nipping force and, therefore, prevents the needle 10 from vacillating or falling off while the needle is being thrust into the vital tissue (particularly tough tissue). Further, since the chuck 51 opens and closes easily, the attachment or detachment of the needle 10 and the adjustment of the length of protrusion thereof (for alteration of the position of the needle 10 to be held) can be easily carried out.

The revolving means 6 and the open-close means 7 which are used for altering the postures of the first and the second needle retaining members 3 and 4 will be described. The revolving means 6 comprises the rotary body 61, wires 62a and 62b, and a manipulating dial 63.

Figure 8:
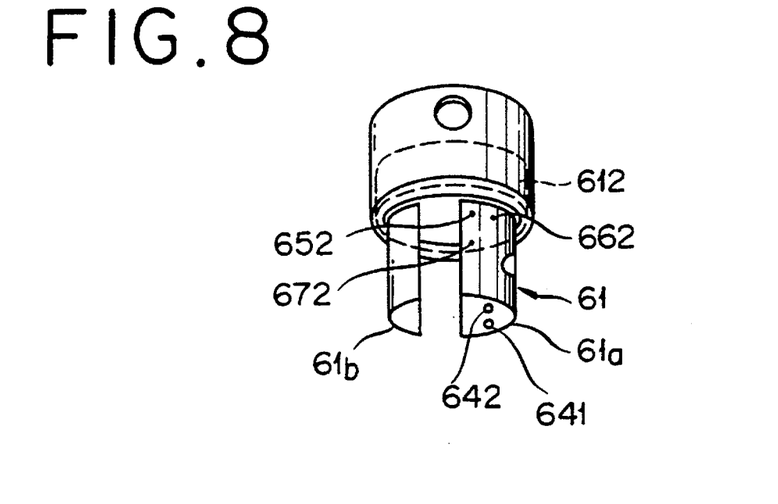
FIG. 8 is a perspective view of a revolving body forming rotary means.

The rotary body 61, as shown in FIG. 2 and FIG. 8, is provided with two supporting pieces 61a and 61b. The connecting parts 32 and 42 of the first needle retaining member 3 and the second needle retaining member 4 are inserted between the two supporting pieces 61a and 61b and are shakeably supported by means of a pin joint.

Figure 10:
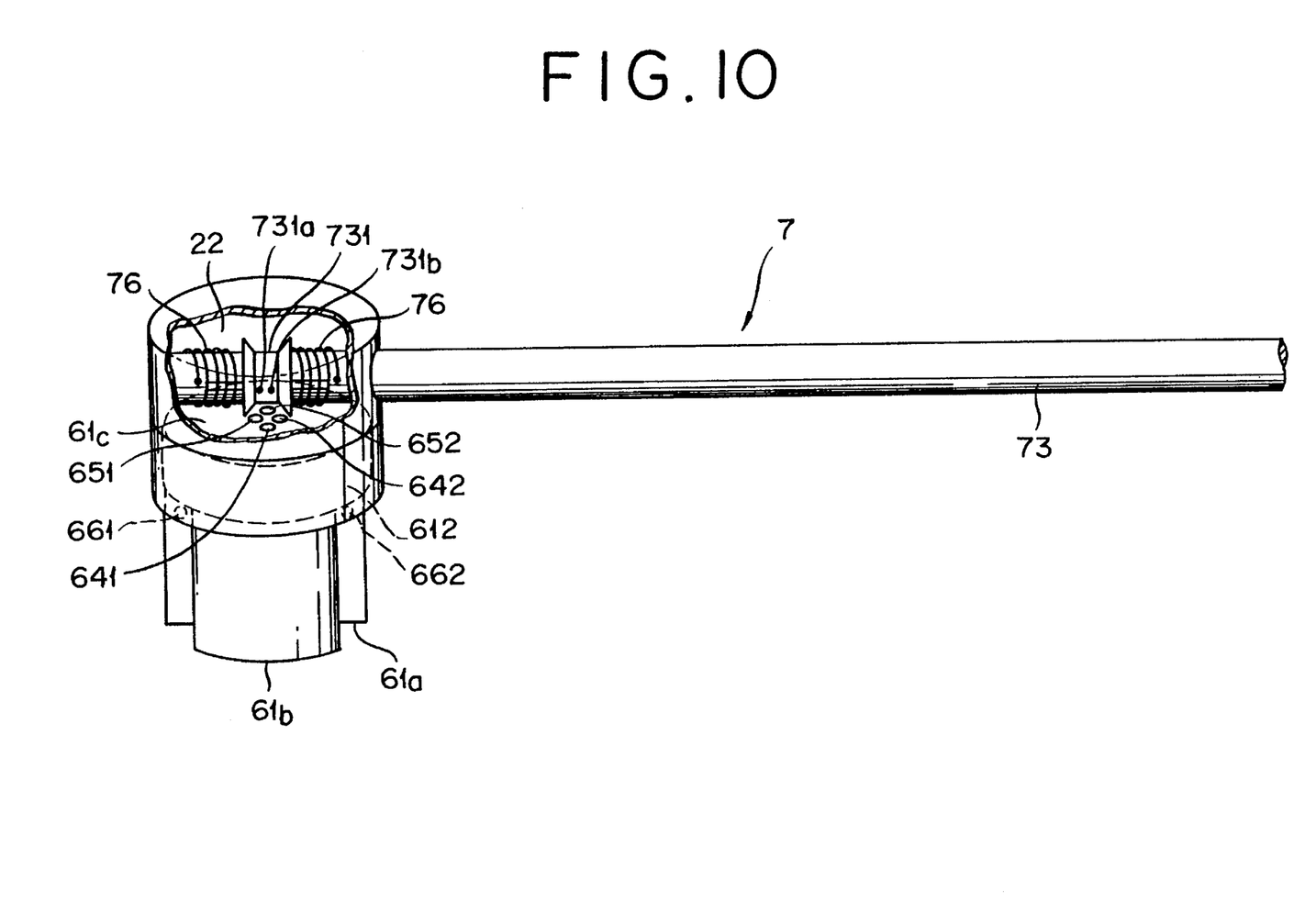
FIG. 10 is a perspective view showing the upper construction of a winding lever and a revolving body forming open-close means.

In the supporting piece 61a, holes for passing wires are formed as shown in FIG. 10. Wires 71 for constructing the open-close means 7 specifically mentioned hereinbelow (actuated when the needle retaining members 3 and 4 are caused to assume the "close" posture) are inserted through holes 641 and 642 extended from the bottom surface of the supporting piece 61a through an upper surface 61c of the rotary body 61. Wires 72 for constructing the open-close means 7 (actuated when the needle retaining members 3 and 4 are caused to assume the "open" posture) are inserted through holes 651 and 652 formed in the opposite end parts of the lateral surface (positioned near the first needle retaining member 3 and the second needle retaining member 4).

Holes 661 and 662 which are disposed inside the holes 651 and 652 communicate with a surface in which the supporting piece 61a is opposed to the supporting piece 61b and allow passage therethrough of the second wire 562 forming the attach-detach means 5. Then, below the holes 651 and 652, connecting parts 671 and 672 (see FIG. 2) permitting connection thereto of the wires 62a and 62b (see FIG. 9) possessed by the revolving means 6 are disposed.

The rotary body 61 which is constructed as described above assumes a generally cylindrical shape. The upper part 612 thereof having a larger diameter is accommodated as rotatably supported within a storage part 22 disposed in the leading end part of the insertion lever 2. The first needle retaining member 3 and the second needle retaining member 4, therefore, are supported rotatably together with the rotary body 61 relative to the insertion lever 2.

Figure 9:
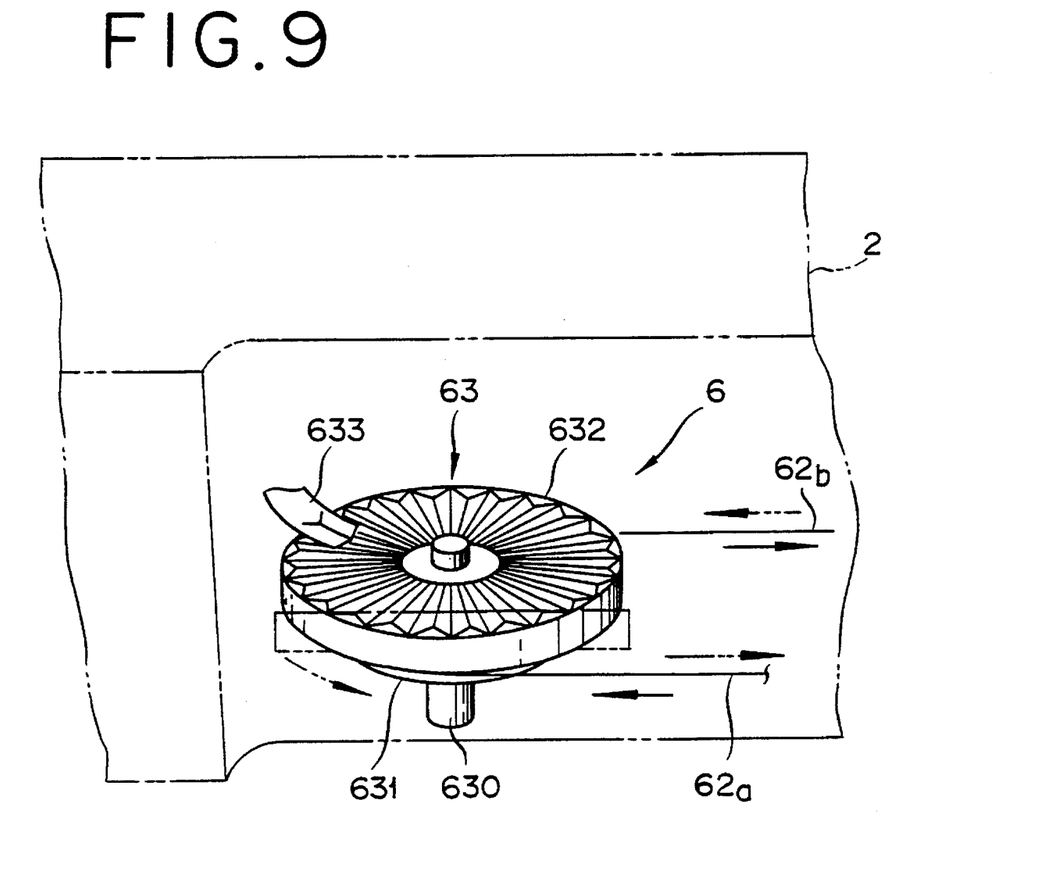
FIG. 9 is a magnified perspective view of a manipulating dial forming the revolving means.

The wires 62 connected at each end to the connecting parts 671 and 672 are passed through a hole 212 formed in the leading end part of the insertion lever 2 and wound round the manipulating dial 63 disposed inside the manipulating part 8 of the insertion lever 2. The manipulating dial 63 which is an angle setting mechanism, as shown in FIG. 9, is supported rotatably by a shaft 630 which is supported inside the insertion lever 2. Part of the outer periphery of the manipulating dial 63 protrudes to the exterior. Thus, the manipulating dial 63 is rotated by having the protruding part thereof manipulated with finger tips. The manipulating dial 63 is provided on the lower side thereof with a winding part 631 for taking up the wire 62. The winding part 631 is rotated jointly with the manipulating dial 63.

The upper surface of the manipulating dial 63 forms a corrugation 632. A positioning member 633 supported on the insertion lever 2 side is held in contact with the corrugation 632. This positioning member 633 is formed of such an elastic material as a leaf spring. The leading end part of the positioning member 633, therefore, is caused to offer resistance to the rotation of the manipulating dial 63 when it is urged so as to be pressed against the corrugation 632. The ridges in the corrugation 632 are equally spaced. The manipulating dial 63 is positioned where the positioning member 633 is engaged with one particular groove in the corrugation 632. The rotary body 61 is rotated in unit angles corresponding to regular intervals of the ridges in the corrugation 632.

Figure 11:
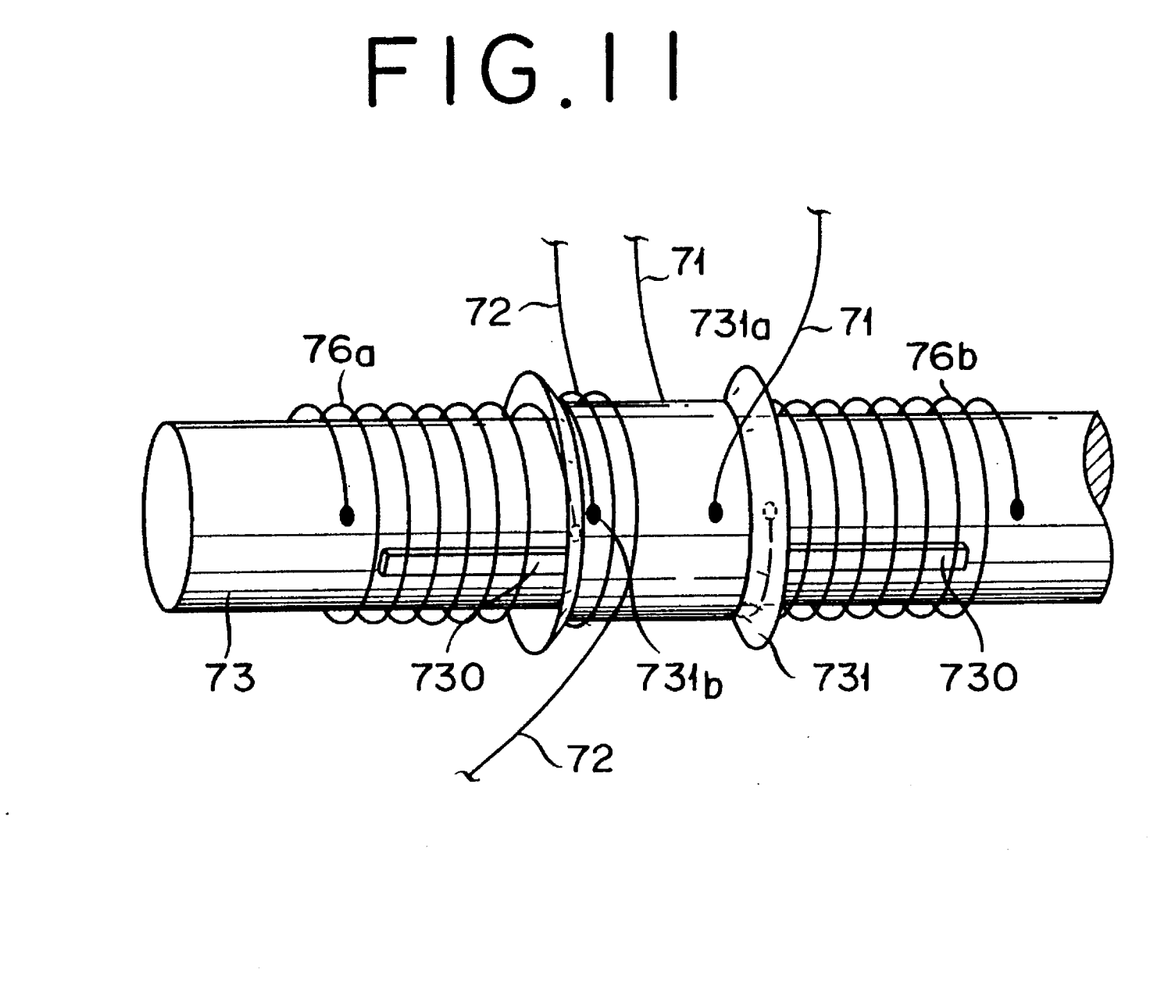
FIG. 11 is a partial perspective view of the winding lever showing the construction of a winding member of the winding lever and the state of a wire taken up on the winding member.
Figure 12:
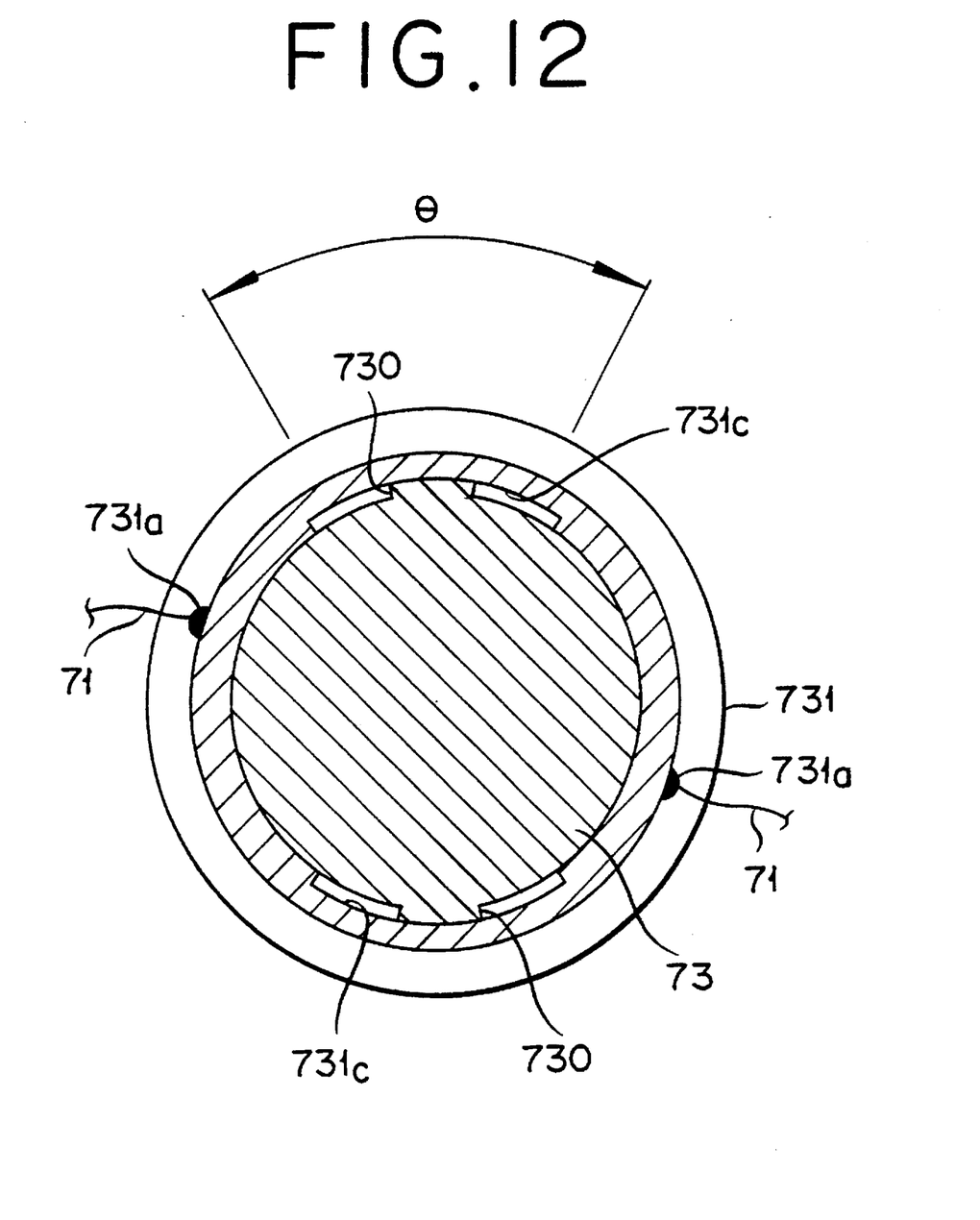
FIG. 12 is a lateral cross section of the winding lever and the winding member.

The open-close means 7, as shown in FIGS. 10 through 15, is provided with the wires 71 and 72, the winding lever 73, a manipulating gear 74, and a ratchet mechanism 75 for regulating the rotation of the manipulating gear 74. The leading end part of the winding lever 73, as shown in FIG. 10, is inserted into the accommodating part 22 of the insertion lever 2. A winding member 731 is formed in the part of the winding lever 73 which is inserted into the accommodating part 22. The winding member 731, as shown in FIG. 11 and FIG. 12, has a cylindrical shape. On the outer peripheral surface of the winding member 731, two pairs of wire fixing parts 731a and 731b possessed of paired stationary parts are formed on the mutually opposite sides. At the opposed positions on the inner peripheral surface of the winding member 731, a pair of grooves 731 (see FIG. 12) are formed along the axial direction.

On the outer peripheral surface of the winding lever 73, as shown in FIG. 11 and FIG. 12, a guide part 730 is continuously formed along the axial direction. This guide part 730 is positioned inside a groove 731c. Then, the winding member 731 is so adapted as to produce a motion in the axial direction along the guide part 730 and further to produce a revolution within an angle (θ) in which the guide part 730 is movable within the groove 731c.

In the leading end part of the winding lever 73, as shown in FIG. 10 and FIG. 11, spring 76a and 76b are interposed between the winding lever 73 and the winding member 731. The springs 76a and 76b are wound on the outer side of the winding lever 73 as fixed on one end side to the winding lever 73 and on the other end side to the winding member 731. By the balance of the urging forces of the two springs 76a and 76b, the winding member 731 is positioned at the upper center part of the rotary body 61. The ends of the wires 71 and 72 are fixed respectively to the wire fixing parts 731a and 731b. These wires 71 and 72 are wound in mutually opposite directions on the winding member 731.

The wire 71, as shown in FIG. 2, is adapted to be actuated when the pair of needle retaining members 3 and 4 are operated in the direction of assuming the "close" posture. One end of this wire 71 is passed through the hole 641 and connected to the flange 311 of the first needle retaining member 3 and the other end thereof is passed through the hole 642 and connected to the main body 41 of the second needle retaining member 4.

The wire 72 is adapted to be actuated when the pair of needle retaining members 3 and 4 are operated in the direction of assuming the "open" posture. One end of this wire 72 is passed through the hole 651 and connected to the flange 311 of the first needle retaining member 3 and the other end thereof is passed through the hole 652 and connected to the main body 41 of the second needle retaining member 4.

Figure 13:
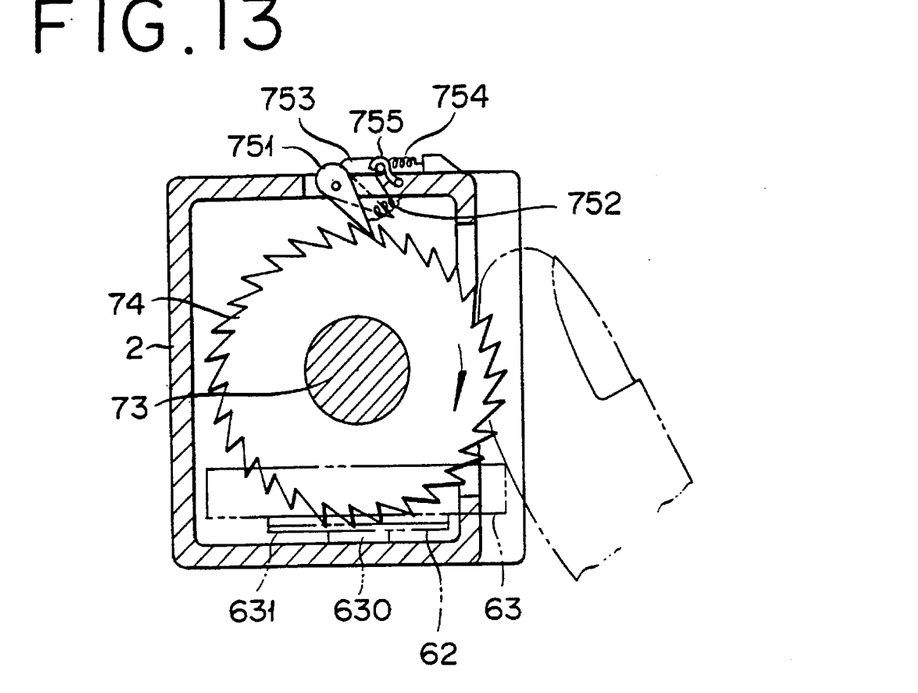
FIG. 13 is a lateral cross section of an insertion lever showing a manipulating gear forming the open-close means.

The winding lever 73 passes along the interior of the insertion lever 2 and reaches the basal end part of the insertion lever 2. In the basal end part of the winding lever 73, the manipulating gear 74 is fixed. The manipulating gear 74, as shown in FIG. 13, has part of the outer peripheral surface thereof protrudes outside the insertion lever 2. The manipulating gear 74 can be rotated by having the protruding part thereof to be manipulated with finger tips. A ratchet mechanism 75 intended for retention of the posture is disposed near the manipulating gear 74. This ratchet mechanism 75 is positioned above the manipulating gear 74 and disposed on the insertion lever 2. An engaging claw 751 is shakeably supported on the insertion lever 2. A spring 752 is interposed between the engaging claw 751 and the insertion lever 2. The leading end of the engaging claw 751 is urged in the direction of the manipulating gear 74.

Figure 14:
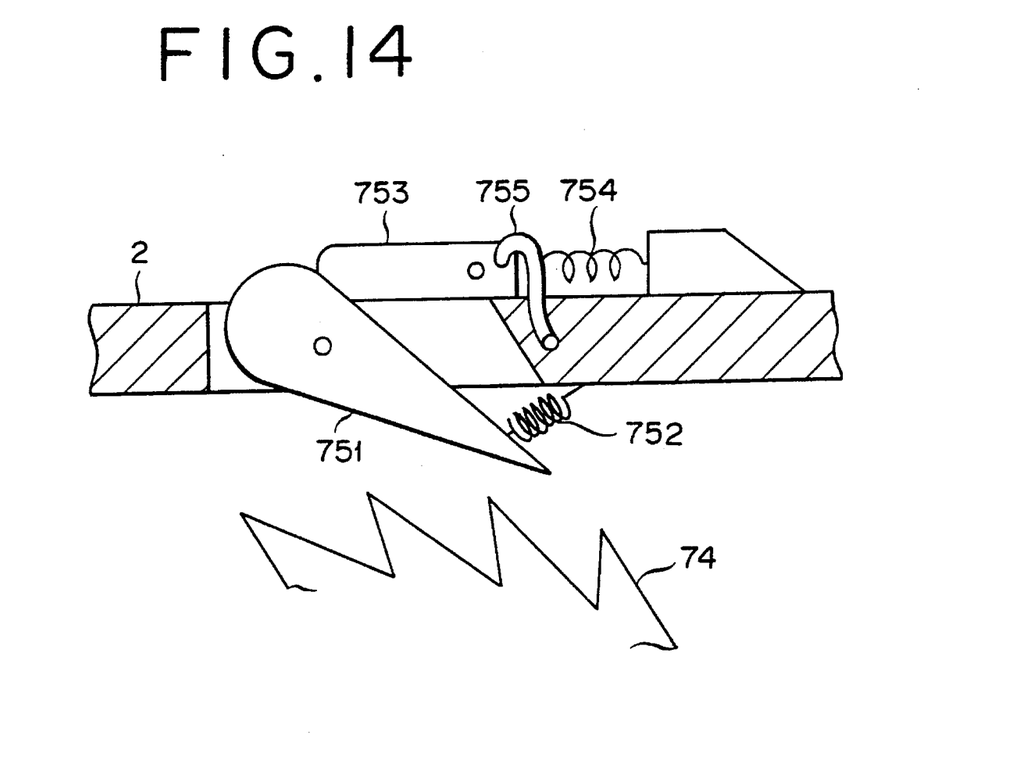
FIG. 14 is a magnified lateral cross section of the insertion lever showing a ratchet mechanism.
Figure 15:
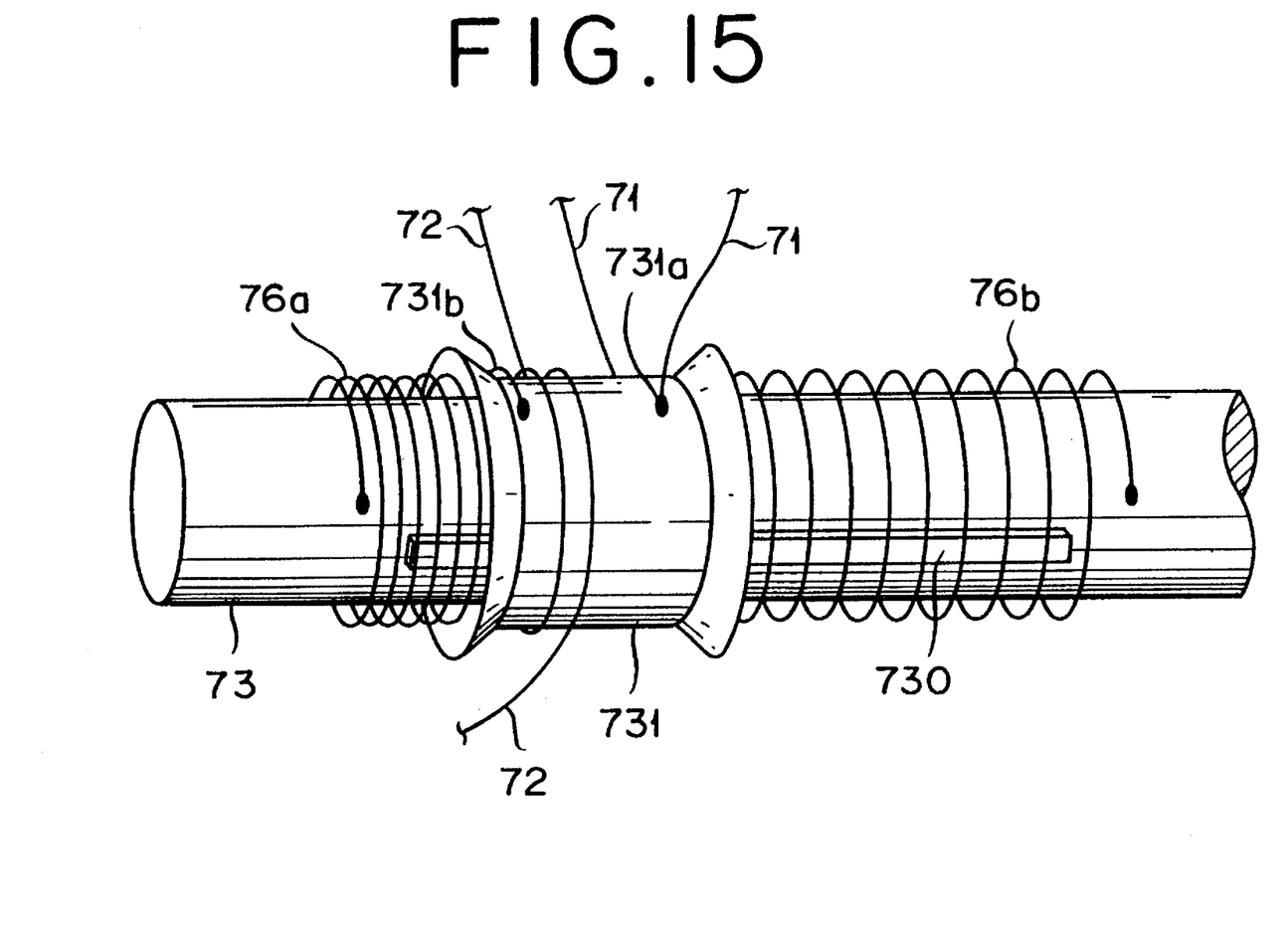
FIG. 15 is a partial perspective view showing the winding member in a state of motion following the revolution of the revolving body.

The basal end of the engaging claw 751, as shown in FIG. 14, protrudes outside the insertion lever 2. A colliding member 753 is disposed slidably in the vicinity of the protruding part of the engaging claw 751. The colliding member 753 is urged by a spring 754 in the direction of the engaging claw 751. The motion of the colliding member 753 is regulated by a locking member 755. By relieving the locking member 755, the engaging claw 751 is separated from the manipulating gear 74 and the manipulating gear is allowed to rotate freely.

By the engaging claw 751 mentioned above, the manipulating gear 74 is allowed to rotate in one direction and prevented from rotating in the other direction (the direction in which the manipulating gear 74 is rotated when the needle retaining members are operated in the direction of assuming the "open" posture).

In the open-close means 7 constructed as described above, when the winding lever 73 is set to rotating, the guide part 730 collides against the inner wall surface of one of the grooves 731c and the winding member 731 rotates in conjunction with the winding lever 73 and winds one of the wires 71 and 72 and unwinds the other wire. Even when the positions of the holes 641, 642, 651 and 652 are moved in consequence of the rotation of the rotary body 61, the possibility that the winding member 731 will revolve and/or move in the axial direction and the wires 71 and 72 will entangle with each other as a consequence is repressed. Further, by the resilient forces of the springs 76a and 76b, the wires 71 and 72 are enabled to remain in a state of proper tension.

The manipulating components of the attach-detach means 5, the revolving means 6 and the open-close means 7 are gathered as described above in the manipulating part 8 which is disposed in the basal end part of the insertion lever 2 so that the insertion lever 2 may be manipulated from outside the trocar, namely the suturing work in the abdominal cavity may be remotely controlled from outside the abdominal cavity. The manipulating part 8 is provided with a grasping part 81 which is adapted to facilitate the retention of the insertion lever 2 during the operation of the manipulating part 8. The manipulating part 8 is further provided on the left side surface thereof (the lateral surface appearing in FIG. 1) with such manipulating components as the manipulating dial 63. Optionally, these manipulating members may be disposed on the right side surface. The guide parts 566 of the stretching lever 564 of the attach-detach means 5 are disposed one each on the opposite lateral surfaces of the insertion lever 2.

The operations of the components of the suturing device 1 constructed as described above will be explained below. The attach-detach means 5 is actuated by moving the stretching lever 564 in the longitudinal direction. In the construction of the present embodiment, the stretching lever 564 on the left side surface actuates the attach-detach means 5 of the first needle retaining member 3 and the stretching lever on the right side surface (omitted from illustration) actuates the attach-detach means 5 of the second needle retaining member 4. The operation of the attach-detach means 5 of the first needle retaining member 3 will be described hereinbelow by way of example. The attachment of the needle 10 to the first needle retaining member 3 is initiated by drawing the stretching lever 564 in the direction of the trailing end thereof. As a result, the second wire 562 is drawn and the two first wires 561 are simultaneously drawn. In consequence of the traction of the first wire 561, the ring 53 retracts and the chuck 51 opens and the substantial inside diameter of the hole 511 enlarges. Then, the basal end part of the needle 10 inserted into this hole 511 and the stretching lever 564 is moved in the direction of the leading end thereof. By the urging force of the coil spring 55, the needle 10 is infallibly held in place as squeezed by the chuck 51. The desire to keep the chuck 51 in the opened state is fulfilled by fixing the stretching lever 564 with the regulating member 567.

The operations mentioned above are similarly implemented by the attach-detach means 5 of the second needle retaining member 4. Then, the leading end part of the needle 10 is inserted in the attach-detach means 5 of the second needle retaining member 4.

The revolving means 6 is actuated by the rotation of the manipulating dial 63. The manipulating dial 63 is rotated by applying a finger tip to the part of the manipulating dial 63 which protrudes outside the insertion lever 2 and suitably turning the finger tip. By the rotation of the manipulating dial 63, one of the wires 62a and 62b is drawn and the other wire is slacked and the rotary body 61 to which the wires 62a and 62b are connected is rotated in the same direction as that of the rotation of the manipulating dial 63. Since the positioning member 633 is kept in contact with the manipulating dial 63, the rotational position of the rotary body 61 will not readily vary and the possibility that the needle retaining members 3 and 4 will be set accidentally to rotating and inflicting damage on the interior of the abdominal cavity while the rotary body 61 is in operation is nil.

By this revolving means 6, the angle to be formed between the plane containing the needle retaining members 3 and 4 and the insertion lever 2 is adjusted. The state shown in FIG. 1 represents the basic posture which the needle retaining members 3 and 4 assume when they are ready for insertion into the trocar. At this time, the needle retaining members 3 and 4 assume the positions which fall in the axial direction of the insertion lever 2. In preparation for the suturing work, the rotary body 61 is rotated to direct the needle retaining members 3 and 4 perpendicularly to the insertion lever 2 (suturing posture).

The open-close means 7 is actuated by the rotation of the manipulating gear 74. By the rotation of the manipulating gear 74, the winding lever 73 is set to rotating and one of the wires 71 and 72 is slacked and the other wire is tensed. When the manipulating gear 74 is rotated in the direction of the arrow (clockwise) in FIG. 13, the wire 71 is wound up and the wire 72 is unwound. By the tension of the wire 71, the first needle retaining member 3 and the second needle retaining member 4 are simultaneously swung (driven as interlocked mutually) and the leading end of the needle 10 held in place by the first needle retaining member 3 is abutted to the leading end of the second needle retaining member 4 ("close" posture) as shown in FIG. 5.

The extraction of the suturing device 1 from the trocar is initiated by actuating the colliding member 753 to relieve the engaging claw 751 of engagement. By the actions of springs 77 and 77 which are suspended between the rotary body 61 and the needle retaining members 3 and 4, the needle retaining members 3 and 4 can be easily made to resume their "open" posture.

Now, the functions of the suturing device 1 of this invention will be explained hereinbelow with respect to cases of using the suturing device 1 for sutures by surgical operations to be performed under a peritoneoscope.

[1] After a suture has been passed through the small hole 103 of the needle 10, the stretching lever 564 is actuated in the longitudinal direction to open and close the chuck 51 and allow the basal end part of the needle 10 to be nipped by the chuck 51.

[2] The needle retaining members 3 and 4 are readied in the basic posture and the suturing device is inserted with the leading end side thereof on the lead into the trocar (not shown).

[3] After the needle retaining members 3 and 4 have protruded from the leading end of the trocar into the abdominal cavity and then reached the site of treatment, by rotating the manipulating dial 63 the wire 62 is drawn to rotate the needle retaining parts 3 and 4 until they assume postures practically perpendicular to the insertion lever 2.

[4] The stretching lever 564 positioned on the right side surface of the insertion lever 2 is drawn to open the attach-detach means 5 of the second needle retaining member 4 and, in the ensuant state of the suturing device 1, the regulating member 567 is actuated to fix the attach-detach means 5 in the "open" state.

[5] The manipulating gear 74 is rotated to actuate the needle retaining members 3 and 4 toward the "close" direction and cause the leading end part of the needle 10 to plunge into the vital tissue. In this case, the insertion lever 2, when necessary, may be rotated. The needle 10 easily pierces the vital tissue since the manipulating gear 74 is prevented from rotating backward by the ratchet mechanism 75 and, consequently, the first needle retaining member 3 is not allowed to move in the "open" direction. Further, since the second needle retaining member 4 is swung synchronously with the first needle retaining member 3 and caused to support the part of the vital tissue for extraction of the needle 10 from the opposite side, the needle can be easily extracted from the vital tissue.

[6] In cases where the depth and the width of the vital tissue subjected to the suturing work are so large that the piercing length of the needle 10 is not sufficient, the protruding length of the needle 10 can be increased by opening and closing the chuck 51 of the first needle retaining member 3 and altering the position at which the needle 10 is nipped by the chuck 51.

[7] After the leading end 102 of the needle 10 has protruded (exposed) to a stated length from the site of extraction, the manipulating gear 74 is actuated to insert the leading end 102 of the needle 10 into the hole 511 of the attach-detach means 5 in the second needle retaining member 4.

[8] After the fixation of the stretching lever 564 by the regulating member 567 has been relieved, the chuck 51 is tightened until it takes hold of the leading end part of the needle 10, the stretching lever 564 is drawn backward and caused to release the needle 10, and the regulating member 567 is actuated to fix the needle 10.

[9] After the engagement of the manipulating gear 74 with the engaging claw 751 has been relieved, the manipulating gear 74 is rotated in the reverse direction and the needle retaining members 3 and 4 are consequently caused to assume their "open" posture. At this time, the needle 10 held in place by the second needle retaining member 4 is extracted from the vital tissue.

[10] The manipulating dial 63 is again rotated in the reverse direction to return the needle retaining members 3 and 4 to their basic posture and extract the insertion level from the trocar. This completes the procedure for the suturing work. The suture passed through the small hole 103 slips off the small hole during the extraction of the suturing device 1 and remains in the body cavity thereafter.

According to the suturing device of this invention, the trouble such as the accidental drop of the needle during the operation of the suturing device is precluded because the leading end of the needle 10 is infallibly held in place by the second needle retaining member 4 while the needle 10 is held in place by the first needle retaining member 3 as described above. Optionally, the manipulating dial 63 may be provided with a construction which resembles the ratchet mechanism 75 disposed in the manipulating gear 74.

The suturing device of this invention does not need to be limited to that which is contemplated by the embodiment cited above. For example, the constructions of the attach-detach means, the revolving means, the open-close means, and the manipulating part may be substituted by arbitrary constructions possessing similar functions. The first needle retaining member 3 and the second needle retaining member 4 may be so constructed as to be swung independently of each other.

The suturing device of this invention does not need to be limited to applications adapted for surgical operations to be performed under a peritoneoscope.

As described above, the suturing device of this invention allows the suturing work to be carried out very quickly because it is provided with two needle retaining members and consequently enabled to perform both the insertion of a needle into the vital tissue and the extraction of the needle from the vital tissue without requiring a change in the posture in which the needle is held by the needle retaining member.

Particularly, when the suturing device is so constructed that the second needle retaining member is allowed while kept abutted to a needle held in place by the first needle retaining member to take hold of the leading end part of the needle, the efficiency of the suturing work by the use of this suturing device is further exalted because the insertion of the needle into the vital tissue and the extraction of the needle from the vital tissue can be carried out continuously.

When the attach-detach means is formed of a chuck which is composed of nipping pieces, the work of attaching and detaching a needle is carried out easily and the retention of the needle is attained infallibly.

When the suturing device is so constructed that the angles of the needle retaining members relative to the insertion lever may be adjusted by the use of the revolving means, the needle retaining members can be easily inserted into and extracted from the trocar and can be made to assume postures most suitable for the suturing work.

When the needle retaining members are formed in an arcuate shape, they allow free adjustment of the length of an arcuate needle to be retained.

When the suturing device is so constructed that the first needle retaining member and the second needle retaining member may be simultaneously opened or closed the insertion of a needle into the vital tissue and the extraction of the needle from the vital tissue can be easily carried out and the transfer of the needle from the first needle retaining member to the second needle retaining member can be effected easily and quickly because the site for extraction can be held down firmly by the second needle retaining member while the insertion of the needle into the vital tissue is in process.

We claim:

1. A suturing device comprising:

an elongate insertion lever to be inserted into a communicating tube for establishing communication between the interior and the exterior of the body cavity, said insertion lever having a leading end part and a basal end part, a first needle retaining member disposed at the leading end part of said insertion lever and provided in the leading end part thereof with attach-detach means detachably holding a basal end part of an arcuately curved needle, a second needle retaining member disposed in the leading end part of said insertion lever and provided in the leading end part thereof with attach-detach means capable of detachably holding the basal end part of said needle, revolving means for revolving each of said needle retaining members at an angle within a stated range relative to said insertion lever, open-close means for switching a posture of each of said first needle retaining member and said second needle retaining member between an "open" posture permitting the respective needle retaining member to be inserted into said communicating tube and a "close" posture permitting a leading end of said needle held by said first needle retaining member to be positioned near the leading end of said second needle retaining member, and a manipulating part disposed in the basal end part of said insertion lever and adapted to manipulate said needle retaining members, said revolving means, and said open-close means by remote controls, said attach-detach means of said second needle retaining member being adapted to hold in place the leading end of the needle held in place by said attach-detach means of said first needle retaining member while said second needle retaining member is in said "close" posture, said needle retaining members each being formed in an arcuate shape and assuming a practically circular shape while they are in the "close" posture for holding in place the needle.

2. A suturing device according to claim 1, wherein said first needle retaining member and said second needle retaining member are opened and closed as mutually interlocked.

3. A suturing device according to claim 1, wherein said attach-detach means is composed of a chuck consisting of a plurality of nipping pieces capable of radial divergence and convergence, urging means for urging said chuck in the closing direction, and stretching means for stretching said chuck in the opening direction by overcoming the urging force of said urging member.

4. A suturing device according to claim 1, wherein said open-close means is provided with wires connected severally to said first needle retaining member and said second needle retaining member, a winding member for taking up said wires, and a winding lever adapted to be inserted into said insertion lever.

5. A suturing device according to claim 4, wherein said open-close means is provided with a posture retaining mechanism for regulating the revolution of at least said first needle retaining member in the direction from said "close" posture to said "open" posture.

6. A suturing device according to claim 1, wherein the radius of curvature of the arc of said needle is about 0.5 to 1.5 times the inside diameter of said communicating tube.

7. A suturing device comprising:

an elongate insertion lever to be inserted into a communicating tube for establishing communication between the interior and the exterior of the body cavity, the insertion lever having a leading end part and a basal end part, a first needle retaining member disposed at the leading end part of said insertion lever and provided in the leading end part thereof with attach-detach means detachably holding a basal end part of an arcuately curved needle, a second needle retaining member disposed in the leading end part of said insertion lever and provided in the leading end part thereof with attach-detach means capable of detachably holding the basal end part of said needle, revolving means for revolving each of said needle retaining members at an angle within a stated range relative to said insertion lever, open-close means for switching a posture of each of said first needle retaining member and said second needle retaining member between an "open" posture permitting the respective needle retaining member to be inserted into said communicating tube and a "close" posture permitting the leading end of said needle held by said first needle retaining member to be positioned near the leading end of said second needle retaining member, and a manipulating part disposed in the basal end part of said insertion lever and adapted to manipulate said needle retaining members, said revolving means, and said open-close means by remote control, said revolving means being adapted to rotate the first needle retaining member which assumes the basic posture in which the segment connecting the opposite ends of the needle held in place by said first needle retaining member runs along the axial line of said insertion lever and a posture in which the segment connecting the opposite ends of the needle held in place by said first needle retaining member runs practically perpendicularly to the axis of said insertion lever.

8. A suturing device according to claim 7, wherein said revolving means is provided with a fixed angle setting mechanism capable of setting angles of rotation at fixed intervals.

* * * * *

UNITED STATES PATENT AND TRADEMARK OFFICE
CERTIFICATE OF CORRECTION

PATENT NO. : 5,603,718
DATED : February 18, 1997
INVENTOR(S) : Zhongren XU

It is certified that error appears in the above-indentified patent and that said Letters Patent is hereby corrected as shown below:

In Column 8, line 48, after "10" and before "inserted", insert -- is --.

In column 12, line 6, delete "controls" and insert -- control --.

Signed and Sealed this

Twentieth Day of May, 1997

Attest:

BRUCE LEHMAN

Attesting Officer      Commissioner of Patents and Trademarks